United States Patent [19]

Takenosita et al.

[11] Patent Number: 5,047,576
[45] Date of Patent: Sep. 10, 1991

[54] POLYMERIZABLE VINYL COMPOUND HAVING POLYTHIOETHER SKELETON

[75] Inventors: Yoichiro Takenosita; Haruo Yoshida, both of Oita, Japan

[73] Assignee: Showa Denko Kabushiki Kaisha, Tokyo, Japan

[21] Appl. No.: 172,178

[22] Filed: Mar. 23, 1988

[30] Foreign Application Priority Data

Mar. 25, 1987 [JP]  Japan .................................. 62-69147
Mar. 26, 1987 [JP]  Japan .................................. 62-70471

[51] Int. Cl.$^5$ .......................................... C07C 321/12
[52] U.S. Cl. ...................................... 560/125; 560/154; 564/153; 564/154
[58] Field of Search ...................... 560/125, 152, 154; 564/153, 154

[56] References Cited

U.S. PATENT DOCUMENTS 2,575,195  11/1951  Smith, Jr. ............................ 560/152
3,853,728  12/1974  Wrzesinski ......................... 525/350

OTHER PUBLICATIONS

Chem. Abst. 108, 187862w.

Primary Examiner—Christopher Henderson
Attorney, Agent, or Firm—Sughrue, Mion, Zinn, Macpeak & Seas

[57] ABSTRACT

A liquid polymerizable prepolymer having good storage stability is prepared by addition reaction of a polyene compound having a group

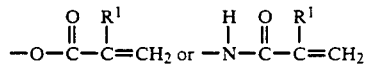

($R_1$=H or $CH_3$) with a polythiol compound in the presence of a basic catalyst under such a condition that the ratio of the total number of vinyl groups to the total number of thiol groups is at least 2. The liquid polymerizable prepolymer is used alone or in combination with an aliphatic polyfunctional vinyl monomer having a refractive index of at least 1.45 for the manufacture of an optical element.

6 Claims, No Drawings ized by cast-polymerizing a composition comprising a monomer having an aromatic ring and/or a halogen atom as the molecule-constituting unit. This process is disclosed in, for example, Japanese Unexamined Patent Publications No. 57-28,115, No. 57-28,116, No. 59-184,210, No. 60-7,314, No. 60-179,406, No. 60-217,301, No. 60-186,514, No. 60-166,307 and No. 60-103,301.

POLYMERIZABLE VINYL COMPOUND HAVING POLYTHIOETHER SKELETON

BACKGROUND OF THE INVENTION

(1) Field of the Invention

The present invention relates to a polymerizable vinyl compound having a polythioether skeleton, which has an excellent storage stability, more particularly, which provides a homogeneous polymer having a good stability against oxidation, and to a process for the preparation thereof.

The present invention also relates to an optical element having an excellent light resistance, which is made from the above-mentioned polymerizable vinyl compound having a polythioether skeleton.

(2) Description of the Related Art

Radical reaction between an olefin compound and a thiol compound is known as the reaction for the synthesis of a thioether, and polymerization of both components is also known wherein a polyfunctional olefin compound and a polyfunctional thiol are polymerized. For example, Otsu et al tried to react bismethacrylamide with dithiol and they found that polymerization by normal addition is advanced in the presence of a radical initiator or basic catalyst but polymerization by abnormal addition is advanced in the presence of an acidic catalyst Kogyo Kagaku Zasshi, 69, 2, 340 (1966). Furthermore, Japanese Examined Patent Publication No. 53-28,959, Japanese Unexamined Patent Publication No. 57-125,025, Japanese Unexamined Patent Publication No. 57-130,572 and Japanese Unexamined Patent Publication No. 53-134,096 disclose polymerization reaction of a polyene compound and a polythiol compound in the presence of a radical initiator or under irradiation with active energy rays such as ultraviolet rays.

However, these conventional techniques involve the following problem. Namely, by the action of the thiol group as a chain transfer agent, polymerization is advanced even during storage in the dark place. Especially in the case where the polyene compound is a derivative of acrylic acid or methacrylic acid, vinyl polymerization of the polyene compound is liable to occur in addition to the radical addition reaction between the polyene compound and polythiol compound. Accordingly, the thiol group is often left in the product.

In the case where it is intended to finally obtain a polymerized cured product, in the abovementioned process, the polymerization conversion is reduced, and because of insufficient curing of the polymerized cured product, new problems of reduction of the hardness, reduction of the solvent resistance and brittleness arise. Moreover, this process has a problem in that because of the difference of the copolymerizability between the polyene compound and polythiol compound, a heterogeneous cured product is readily obtained when a molded article having a large thickness is prepared. This heterogeneity leads to formation of streaks which shape differs according to the conditions. Especially when the cured product is used as a homogeneous transparent resin, the appearance characteristics are drastically degraded. For example, when the cured product is used for an optical disc or the like, an erroneous operation is caused at the recording or reading step. Moreover, in the case of a spectacle lens or the like, since the heterogeneity is observed by the naked eye, there arise problems of reduction of the visual power and reduction of the commercial value.

In the case where a composition comprising a polyene compound and a polythiol compound is used as the polymerizable monomer composition, as pointed out hereinbefore, if the thiol group is left, the storage stability is degraded and undesirable phenomena occur due to the heterogeneity at the polymerization step and the problem of an unstability of the cured product against oxidation arises. A coating treatment with a reflection-preventing film is sometimes carried out for reducing the light reflection of the cured product. This coating treatment is ordinarily performed by vacuum deposition of $SiO_2$ or $Al_2O_3$ at a high temperature under vacuum. At this coating treatment, if the thiol group is left on the surface of the cured product, the surface undergoes oxidation, and coloration or surface roughening occurs. In some applications, the cured product is exposed outdoors. Also in this case, the remaining thiol group is oxidized, and coloration or surface roughening occurs.

In order to provide organic glasses, use of resins having a high refractive index has been tried. However, resins having a high refractive index, for example, polystyrene (refractive index = 1.59) and polycarbonate (refractive index = 1.59), are thermoplastic resins, and since they are molded usually by injection molding, the strain is often left after molding. Moreover, these resins have a poor solvent resistance.

As the means for overcoming these defects of the molding material and molding method, there has been proposed a process in which a resin having a high refractive index is prepared by cast-polymer- However, a resin having a high refractive index, prepared according to this process, is poor in the light resistance, and the resin has a problem in that if the resin is exposed outdoors for a long time, the resin is colored into yellow to brown by sunlight. In the field where prevention of coloration is required, for example, when the resin is used for a spectacle lens or the like, this problem reduces the commercial value. Moreover, when the deterioration is extreme, cracks are formed on the surface of the resin and fogging or whitening is caused to occur.

As another means for increasing the refractive index, introduction of a sulfur compound as the molecule-constituting unit has been tried. For example, Japanese Unexamined Patent Publication No. 57-158,213 discloses a polymer having a high refractive index, which comprises a thioester of acrylic acid or methacrylic acid as a comonomer. Although the polymer obtained according to this process has a high refractive index, the polymer is thermoplastic and is not satisfactory in heat resistance and chemical resistance. Moreover, a polymer having a diphenylsulfone structure (see, for example, Japanese Unexamined Patent Publications No. 57-28,118, No. 57-147,505 and No. 61-108,616), a polymer having a diphenyl sulfide structure (see, for example, Japanese Unexamined Patent Publication No. 60-26,010) and a polymer having a dibenzyl sulfide structure (see, for example, Japanese Unexamined Patent Publication No. 59-164,501) have been proposed.

However, monomers used in these proposals have generally poor compatibility with other liquid monomers and their molding is difficult. Moreover, the obtained resins having a high refractive index possess poor light resistance and coloration is easily caused.

Since an aliphatic sulfide compound is excellent in the light resistance, for example, a sulfide compound having a low molecular weight is used as an antioxidant for a resin, and a sulfide compound having a high molecular weight is frequently used as a sealing material for windowpanes. Furthermore, it is reported that a high-molecular-weight sulfide compound obtained by radical-polymerizing a polyene compound/polythiol compound by a radical initiator or chemically active energy rays such as ultraviolet rays is used as a printing material, a paint, an adhesive, a molding material or the like (see Japanese Examined Patent Publication No. 53-28,959 and Japanese Unexamined Patent Publication No. 57-125,207).

However, if a polyene compound composed of an acrylic or methacrylic acid derivative is used in this process, since the reactivity of a composition comprising the polyene compound/polythiol compound is high, the storage stability is very low. Moreover, since homopolymerization of the vinyl group of the polyene compound and radical addition reaction of the polyene compound/polythiol compound are simultaneously advanced, the mercapto group of the polythiol compound is liable to remain. Because of this undesirable reaction, the crosslinking density is reduced at polymerization and curing of the polymer is insufficient. Therefore, new problems of reduction in hardness, solvent resistance and strength arise. Furthermore, in the field of a spectacle lens or the like where homogeneity and transparency are required, because of the difference of the reactivity between the polyene compound and polythiol compound, abrupt change of the refractive index in a narrow region, so-called "polymerization unevenness", often occurs, and the optical characteristic or appearance is drastically degraded. If the polymer is used as an optical disc material, an erroneous operation is caused at the recording or reading step because of these problems.

Thus, when a conventional composition comprising a polyene compound and a polythiol compound is used as the polymerizable monomer composition for an optical material, the storage stability is poor and the problem of "polymerization unevenness" cannot be solved.

SUMMARY OF THE INVENTION

It is a primary object of the present invention to overcome the defects of the above-mentioned conventional polymerizable composition comprising a polyene compound and a polythiol compound and provide a polymerizable vinyl compound having a polythioether skeleton, which has a good storage stability and provides a homogeneous cured product having a good stability against oxidation by polymerization.

Another primary object of the present invention is to provide an optical element having an excellent light resistance and no polymerization unevenness, which has a refractive index of 1.51 to 1.53 and an Abbe number larger than 50.

In one aspect of the present invention, there is provided a polymerizable vinyl compound having a polythioether skeleton, which is prepared by additionreacting (1) a polyene compound represented by the following general formula (I):

$$A\text{-}X_m \text{ or } Y_n\text{-}D\text{-}X_p \qquad (I)$$

wherein X stands for (a)

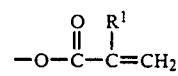

or (b)

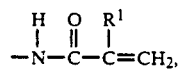

Y stands for (c)

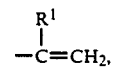

A and D stand for a polyvalent aliphatic or alicyclic hydrocarbon residue, or

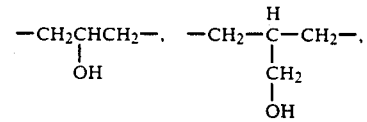

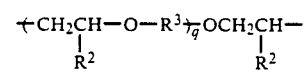

or

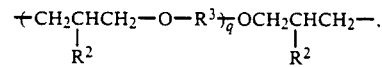

$R^1$ stands for H or $CH_3$, $R^2$ stands for H, an aliphatic hydrocarbon residue or OH, $R^3$ stands for an aliphatic or alicyclic hydrocarbon residue which may contain a halogen atom, and m, n, p and q are integers of m $\geq$ 2, n $\geq$ 1, p $\geq$ 1 and q $\geq$ 1, with (2) at least one polythiol compound selected from the group consisting of those which are represented by the following general formulae (II) and (IV):

wherein $R^4$ stands for an organic group consisting of polyvalent aliphatic or alicyclic hydrocarbons preferably having 2 to 10 carbon atoms, and r is an integer of from 2 to 4,

wherein $R^9$ stands for a substituted or unsubstituted aliphatic polyhydric alcohol residue having 2 to 20 carbon atoms, which may have an OH group, u is an integer of 1 or 2, and v is an integer of from 2 to 4, in the presence of a basic catalyst under such a condition that the ratio of the total number of vinyl groups in the polyene compound (I) to the total number of thiol groups in the polythiol compound (II) and/or (IV) is at least 2; the terminal groups of said polymerizable vinyl compound being selected from the group consisting of X and Y wherein X and Y are the same as defined above.

In another aspect of the present invention, there is provided a process for preparing the above-mentioned polymerizable vinyl compound having a plythioether skelton, which comprises addition-reacting (1) the above-mentioned polyene compound with (2) the above-mentioned polythiol compound in the presence of a basic catalyst under such a condition that the ratio of the total number of vinyl groups in the polyene compound (I) to the total number of thiol groups in the polythiol compound (II) and/or (IV) is at least 2.

In still another aspect of the present invention, there is provided an optical element comprising a cured product of a mixture comprising (A) 50% to 100% by weight of a liquid polymerizable vinyl compound having a polythioether skeleton obtained by addition reaction of (1) a polyene compound represented by the following general formula:

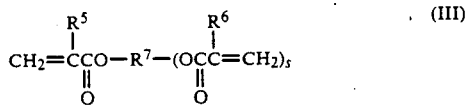 (III)

wherein $R^5$ and $R^6$, which may be the same of different, stand for H or a $CH_3$ group, $R^7$ stands for a substituted or unsubstituted aliphatic polyhydric alcohol residue or substituted or unsubstituted polyalkylene-ether polyol residue having 2 to 20 carbon atoms, which may have an OH group, and s is an integer of 1 or 2, with (2) the above-mentioned polythiol compound of the formulae (II) and/or (IV) in the presence of a basic catalyst under such a condition that the ratio of the total number of groups in the polyene compound (III) to the total number of thiol groups in the polythiol compound (II) and/or (IV) is at least 2, and (B) 0% to 50% by weight of a polymerizable aliphatic polyfunctional vinyl monomer having a refractive index of at least 1.45.

DESCRIPTION OF THE PREFERRED EMBODIMENTS

As typical examples of the polyene compound represented by the general formula (I), there can be mentioned esters such as ethylene glycol diacrylate or dimethacrylate, diethylene glycol diacrylate or dimethacrylate, tetraethylene glycol diacrylate or dimethacrylate, 2-hydroxypropyl-1,3-diacrylate or -dimethacrylate, 1,6-hexane-diacrylate or -dimethacrylate, neopentyl glycol diacrylate or dimethacrylate, pentaerythritol triacrylate or trimethacrylate, trimethylolpropane triacrylate or trimethacrylate, dipentaerythritol hexaacrylate or hexamethacrylate; amides such as ethylene diacrylamide or dimethacrylamide, 1,6-hexane diacrylamide or dimethacrylamide, propyl diacrylamide or dimethacrylamide, 1,4-cyclohexane diacrylamide or dimethacrylamide and bis(4-aminocyclohexyl)methane diacrylamide or dimethacrylamide; and polyenes such as 1,4-($\beta$-acryloyloxyethoxy or -methacryloyloxyethoxy)cyclohexane.

As typical examples of the polythiol compound represented by the general formula (II), there can be mentioned ethanedithiol, propane-1,2-dithiol, n-hexane1,6-dithiol, propane-1,3-dithiol, neopentane-1, 3-dithiol, n-decane-1,10-dithiol, n-dodecane-1, -12-dithiol, 1,3-cyclohexanedithol and 1,4-cyclohexanedithol.

As typical examples of the polythiol compound represented by the general formula (IV), there can be mentioned ethylene glycol dithioglycolate, diethylene glycol dithioglycolate, trimethylolpropane trithioglycolate, trimethylolpropane dithioglycolate, neopentylglycol tetrathioglycolate, pentaerythritol tetrathioglycolate and trimethylolpropane trithiopropionate.

As typical examples of the polyene compound represented by the general formula (III), there can be mentioned esters such as ethylene glycol diacrylate or dimethacrylate, diethylene glycol diacrylate or dimethacrylate, triethylene glycol diacrylate or dimethacrylate, tetraethylene glycol diacrylate or dimethacrylate, 2-hydroxypropyl-1,3-diacrylate or -dimethacrylate, 1,6-hexane-diacrylate or -dimethacrylate, neopentyl glycol diacrylate or dimethacrylate, pentaerythritol triacrylate or trimethacrylate, trimethylolpropane triacrylate or trimethacrylate and dipentaerythritol hexaacrylate or hexamethacrylate.

At the addition reaction between the polyene compound (I) or (III) and polythiol compound (II) and/or (IV), it is indispensable that the ratio of the total number of vinyl groups in the polyene compound (I) or (III) to the total number of thiol groups in the polythiol compound (II) and/or (IV) is at least 2, preferably 2 to 20, and more preferably 2 to 10. For example, if this ratio is lower than 2, for example, in the case where both of the polyene compound and polythiol compound are bifunctional compounds, a linear prepolymer is obtained in the presence of a basic catalyst, but in the case where one of the polyene compound and polythiol compound is a trifunctional compound, gelation often takes place during formation of the prepolymer. Furthermore, polymerization unevenness is easily caused in a cured product obtained by polymerizing the prepolymer, and the polymer has a poor heat resistance. On the other hand, if the above ratio is too large, the prepolymer can be easily formed but the refractive index of a cured product obtained from the prepolymer is liable to be lower than 1.51.

Other copolymerizable vinyl compound can be added to the so-obtained polymerizable vinyl compound having a polythioether skeleton according to need. As the other copolymerizable vinyl compound, there can be mentioned methyl methacrylate and butyl acrylate.

For the subsequent polymerization, the polymerizable vinyl compound having a polythioether skeleton, obtained by the addition reaction between the polyene compound and the polythioether compound, is preferably a liquid having a viscosity of 10 to 30,000 cP at 25° C.

The addition reaction of the polyene compound (I) or (III) with the polythiol compound (II) and/or (IV) is carried out in the presence of a basic catalyst.

Known basic ion-exchange resins, potassium t-butoxide, phosphine compounds and amine compounds can be used as the basic catalyst. A phosphine compound or an amine compound is especially preferred.

As examples of the phosphine compound, there can be mentioned triphenylphosphine, tri-n-butylphosphine and triethylphosphine, and as examples of the amine compound, there can be mentioned pyridine, N,N-dimethylaniline, N,N-diethylaniline, trimethylamine, triethylamine, tri(n-propyl)amine, tri(isopropyl)amine, tri(n-butyl)amine, tri(isobutyl)amine, tri(sec-butyl)amine, dimethylethylamine, diethylmethylamine, triethanolamine, dimethylethanolamine, monomethyldiethanolamine and diethylamine.

These basic catalysts can be used singly or in the form of mixtures of two or more of them. The amount of the basic catalyst used varies according to the kinds, combination and amounts of the polyene compound (I) or (III) and the polythiol compound (II) and/or (IV). In general, the basic catalyst is used in an amount of 0.01 to 3% by weight, preferably 0.03 to 1% by weight, based on the total amount of the polyene compound (I) or (III) and the polythiol compound (II) and/or (IV).

If the amount of the basic catalyst is smaller than 0.01% by weight, no substantial catalytic reaction is exerted, and homopolymerization of the vinyl group of the polyene compound often takes place. On the other hand, even if the basic catalyst is used in an amount exceeding 3% by weight, the effect is not enhanced by the use of a large amount of the basic catalyst, and coloration is caused at the polymerization step. In addition, a large amount of a removing agent is necessary for removing the catalyst after the reaction.

At the addition reaction of the polyene compound with the polythiol compound, a low-boiling-point inert solvent such as benzene, tetrahydrofuran, dioxane or ether can be used in an appropriate amount for removing the reaction heat. However, when the solvent used is removed by heating, gelation is readily caused by homopolymerization of the polyene compound, and therefore, use of a solvent having a high boiling point is not preferred. For preventing gelation, a phenol type or amine type inhibitor can be added, so far as polymerization between the vinyl monomers is not inhibited at the subsequent step.

In the case where it is necessary to remove the basic catalyst after the addition reaction, known means such as adsorption, extraction or vacuum suction can be applied, so far as the subsequent polymerization is not adversely influenced. Adsorption using neutral or acidic alumina or an acidic ion-exchange resin can be especially applied to the removal of the amine compound, and in the case where the amine compound has a low-boiling-point, the removing method utilizing vacuum suction can be adopted.

The addition reaction temperature varies according to the particular combination of the compounds, mixing ratio of the polyene compound with the polythiol compound, and the kind and amount of the basic catalyst. The addition reaction temperature is ordinarily 0 to 100° C. and preferably 20 to 60° C. Even if the addition reaction temperature is higher than 100° C., homopolymerization of the vinyl group of the polyene compound can be prevented by appropriately selecting the kind and amount of the basic catalyst, but gelation often takes place. Even if the addition reaction temperature is lower than 0° C., the addition reaction is advanced, but the reaction speed is low and such a low temperature is not preferred from the viewpoint of the productivity.

In order to prevent formation of a disulfide by autooxidation of the polythiol compound, preferably the addition reaction is carried out in an inert atmosphere.

The so-obtained polymerizable vinyl compound having a polythioether skeleton has a structure in which molecule ends are capped with the polymerizable vinyl group, and the compound is excellent in the storage stability. This polymerizable vinyl compound has a viscosity of 10 to 30,000 cP, preferably 50 to 2,000 cP, at 25° C. and, at a certain charging molar ratio between the polyene compound and the polythiol compound, the polymerizable vinyl compound contains the unreacted polyene compound. This unreacted polyene compound may be removed according to need, or the vinyl compound can be directly used in the state containing the unreacted polyene compound.

Known means such as a method using chemically active energy rays and a method using a radical initiator can be used as means for polymerizing and curing the polymerizable vinyl compound having a polythioether skeleton. These two methods can be adopted in combination.

In the method using active energy rays, there can be used ultraviolet rays, infrared rays and visible rays (radioactive rays) can be used. As the ultraviolet ray source, there can be mentioned a high-pressure mercury lamp and a metal halide lamp. In this method, polymerization can be promoted by addition of a photoinitiator, so far as coloration or other trouble is not caused. For example, benzoin, benzoin methyl ether, benzoin ethyl ether, benzoin propyl ether, benzoin isobutyl ether, benzoin dimethyl ketal 2-hydroxy-2-benzoylpropane, benzyl or diphenyl disulfide can be used in an amount of 0.01 to 5% by weight.

In the method using the radical initiator, as the radical initiator, there can be used azo compounds such as azobisisobutyronitrile, 2,2-azobis(2,4-dimethylvaleronitrile), azobismethylvaleronitrile and azobiscyclohexanecarbonitrile, and peroxides such as benzoyl peroxide, t-butyl peroxide, t-butyl peroxy-2-ethylhexanoate and diisopropyl peroxydicarbonate. Preferably the radical initiator is used in an amount of 0.05 to 5% by weight.

The optical element of the present invention may be composed of a cured product of the above-mentioned liquid polymerizable vinyl compound having a polythioether skeleton, or a cured product of the above-mentioned liquid polymerizable vinyl compound and a polymerizable aliphatic polyfunctional vinyl monomer having a refractive index of at least 1.45, so far as attainment of the object of the present invention is not substantially inhibited.

As the polymerizable aliphatic polyfunctional vinyl monomer having a refractive index of at least 1.45, there can be mentioned, for example, ethylene glycol diacrylate or dimethacrylate, diethylene glycol diacrylate or dimethacrylate, triethylene glycol diacrylate or dimethacrylate, tetraethylene glycol diacrylate or dimethacrylate, 2-hydroxypropyl-1,3-diacrylate or -dimethacrylate, 1,6-hexane-diacrylate or dimethacrylate, neopentyl glycol diacrylate or dimethacrylate, pentaerythritol triacrylate or trimethacrylate, and trimethylolpropane trimethacrylate. A polymerizable aliphatic polyfunctional vinyl monomer having a refractive index lower than 1.45 is not preferred because the refractive index of the cured product is reduced.

The mixing ratio between the liquid polymerizable vinyl compound and the polymerizable aliphatic polyfunctional vinyl monomer is such that the amount of the liquid polymerizable vinyl compound is at least 50% by weight and the amount of the polymerizable aliphatic polyfunctional vinyl monomer is up to 50% by weight. If the amount of the polymerizable aliphatic polyfunctional vinyl monomer is larger than 50% by weight, the refractive index of the cured product is low, and the shrinkage is large at the polymerization step and it is therefore difficult to obtain a cured product which is free of cracks or fissures and has a good appearance.

A yellowing-preventing agent, a leveling agent and an ultraviolet absorber can be added to the liquid polymerizable vinyl compound or the mixture of the liquid polymerizable vinyl compound and the polymerizable aliphatic polyfunctional vinyl monomer according to need, so far as polymerization curing is not disturbed.

A dye, a filler, a pigment, a fluorescent whitener, a polymerizable viscosity reducing agent and a diluent monomer, for example, a monofunctional (meth)acrylate such as hydroxy(meth)acrylate or methyl (meth)acrylate, can also be added to the polymerizable vinyl compound.

The optical element of the present invention is prepared by cast polymerization. A cast polymerization vessel having a plate-like, lens-like, columnar, prismatic, conical or spherical shape and a casting mold or mold frame specially designed according to the intended use are used. For example, an optical lens is prepared by casting the liquid polymerizable vinyl compound or the mixture of the liquid polymerizable vinyl compound and the polymerizable aliphatic polyfunctional vinyl monomer into a casting mold for a lens, which is constructed by a glass mold and a gasket, curing the vinyl compound or the mixture thereof by active energy rays or a combination of these curing means, and taking out the cured product from the mold.

By the optical element provided according to the present invention, there are meant elements exerting an intended function by transmission or reflection of light, for example, lenses for a still camera, a video camera, a telescope and spectacles. optical discs for optical reading, reproduction and writing, such as a If the amount of the basic catalyst is smaller than 0.01% by weight, no substantial catalytic action is compact disc and a video disc, and transparent sealing materials for sealing a display element such as a liquid crystal.

The polymerizable vinyl compound having a polythioether skeleton according to the present invention can be widely used in fields other than optical elements, for example, as a paint, an adhesive, a sealing material, a surface-coating material or a dental composite resin.

The present invention will now be described in detail with reference to the following examples, wherein parts are by weight.

The physical properties of the polymerizable vinyl compound having a polythioether skeleton were determined according to the following methods.

(1) Analysis of Thiol Group

A. Titration Method (Volhard method)

At first, 1 to 2 g of a sample of the polymerizable vinyl compound having a polythioether skeleton was incorporated with 10 ml of toluene and 10 ml of ethanol to be thereby dissolved, and 10 ml of 0.1N aqueous $AgNO_3$ was added to the solution. An iron alum indicator was added, excessive $AgNO_3$ was determined by back titration with 0.025N $NH_4SCN$, and the amount of the residual thiol group was analyzed. From the obtained value, the relative decrease ratio (i.e., conversion) of the thiol group based on the charge was calculated.

B. Raman Spectroscopic Method

In the case of a gelled sample which was not liquid and could not be dissolved in solvents, the analysis was carried out by using the Raman spectroscopy (apparatus: Model R-800 supplied by Nippon Bunko K.K.). The conversion of the thiol group was calculated from the relative decreases of the ratio of the absorption of the thiol group at 1,570 $cm^{-1}$ to the absorption of the carbonyl group at 1,730 $cm^{-1}$, which decrease was relative to that as determined in the monomer state.

(2) Analysis of Vinyl Group

The conversion of the vinyl group was determined according to $^1H$-NMR by using Model R-24B supplied by Hitachi Ltd. in the case where a gel was not formed or gelation was not caused, and according to the Raman spectroscopy in the case of a gelled sample. The conversion of the vinyl group was calculated from the relative decrease of the ratio of the absorption of the vinyl group at about 1,620 $cm^{-1}$ to the absorption of the carbonyl group at about 1,730 $cm^{-1}$, which decrease was relative to the ratio in the monomer state.

(3) Storage Stability

The polymerizable vinyl compound having a polythioether skeleton was allowed to stand in the dark and in the air at a room temperature, and the time required for formation of a gel was measured. The storage stability was evaluated based on this time according to the following scale:

A: at least one month

B: shorter than one month

The physical properties of cured products obtained from the polymerizable vinyl compounds having a polythioether skeleton in the following examples and comparative examples were determined according to the following methods.

(4) Appearance (Polymerization Unevenness)

The appearance of the cured product was observed with the naked eye before a 20-W fluorescent lamp and the cured product was evaluated according to the following scale:

C: unevenness was observed

A: no unevenness was observed (5) Appearance on Formation of Reflection-Preventing Coating Under a pressure of $10^{-6}$ to $10^{-5}$ mmHg and at a temperature of 85 to 120° C., $SiO_2$ was evaporation-deposited in a thickness of 0.4 nm and $Al_2O_3$ was then evaporation-deposited in a thickness of 0.1 nm. Then, the appearance was observed with the naked eye.

(6) Refractive Index

The refractive index was measured at 20° C. by using an Abbe refractometer. Bromonaphthalene was used as the contact liquid.

(7) Hardness

The hardness was measured by using a Barcol hardness meter.

(8) Light Transmission

The light transmission (%) of a plate of a cured product having a thickness of 2 mm was measured at a wavelength of 550 nm.

(9) Impact Resistance

According to the FDA standard, a steel ball having a diameter of 15.9 mm and a weight of 16.2 g was fallen down at the center of a plate of a cured product having a thickness of 2 mm from a height of 127 cm. The impact resistance was evaluated according to the following scale:

A: plate was not broken

C: plate was broken

(10) Heat Resistance

A sample was allowed to stand in a hot air drier at 120° C. for 3 hours, and the heat resistance was evaluated by observation with naked eye according to the following scale:

A: coloration or surface distortion was not found
C coloration or surface distortion was found

(11) Dyeability

A cured product was immersed in a 0.2% aqueous solution of Disperse Brown 3 at 92° C. for 10 minutes, and the cured product was taken out, washed with water and dried. The dyeability was evaluated according to the following scale:

A: no dyeing unevenness was observed
C: slight dyeing unevenness was observed

(12) Light Resistance

A cured product was exposed to a weather-o-meter for 200 hours, and with respect to a test piece having a thickness of 2.2 mm, the yellowing index (YI) was measured by using a color meter (supplied by Suga Shinkenki Seisakusho) according to the method of JIS K-7103. The light resistance was evaluated based on the increase ($\Delta YI$) from YI before the exposure according to the following scale:

A: $\Delta YI°1$
B: $1°\Delta Y <5$
C: $5<\Delta YI$

EXAMPLE 1

A two liter separable flask equipped with a stirrer and a dropping funnel was charged with 700 parts of ethylene glycol dimethacrylate, and 2 parts of diethylamine was added with stirring to form a solution. Then, 300 parts of ethylene glycol dithioglycolate was added dropwise to the solution over a period of 30 minutes. Exothermic reaction occurred by dropwise addition. The dropping speed was adjusted so that the temperature did not exceed 60° C. Then, the reaction mixture was stirred at 40° C. for 10 hours. After termination of the reaction, 50 parts of an inorganic adsorbent for strongly basic adsorption (Kyoward 700SL supplied by kyowa Kagaku Kogyo K.K.) was added to remove diethylamine. The adsorbent was removed by filtration to obtain a liquid product.

The following $^1$H-NMR spectrum data and Raman spectrum data were obtained with respect to the so-obtained liquid product.

$^1$H-NMR:

1.2–1.35 ppm (multiplet, $\alpha$-methyl proton formed by addition of $\beta$-methylene of methacryloyl to thiol), 1.9–2.03 ppm (doublet, $\alpha$-methyl proton of methacryloyl), 2.5–3.1 ppm (multiplet, methine proton and $\beta$-methylene proton adjacent to $\alpha$-methyl proton formed by addition of $\beta$-methylene of methacryloyl to thiol), 3.23–3.33 ppm (methylene proton adjacent to thiol of ethylene dithiopropionate), 4.3–4.5 ppm (ethoxy protons of ethylene glycol dimethacrylate and ethylene dithiopropionate), 5.5–6.2 ppm ($\delta$-methylene proton of methacryloyl)

In the Raman spectrum, the absorption of thiol at 1,570 cm$^{-1}$ disappeared.

The conversion of the vinyl group derived from methacryloyl was 39.2% determined from the integration curve of $^1$H-NMR and this conversion was well in agreement with the theoretical conversion of 39.5% based on the presumption that 100% of the thiol group was reacted. When the thiol group in the liquid product was determined by the titration method, it was found that the conversion of the thiol group was 98.9% and the addition reaction was almost quantitatively occurred.

From the foregoing results, it was obvious that a polymerizable vinyl compound having a polythioether skeleton was obtained.

EXAMPLES 2 THROUGH 6

The addition reaction was carried out in the same manner as described in Example 1 except that the polyene compound, polythiol compound, basic catalyst, addition reaction temperature and addition reaction time were changed as shown in Table 1.

The results showed that polymerizable vinyl compounds having substantially a polythioether skeleton were obtained.

COMPARATIVE EXAMPLES 1 THROUGH 3

The addition reaction were carried out in the same manner as described in Example 1 except that conditions were changed as shown in Table 1. The results are shown in Table 1.

In $^1$H-NMR, a broad peak was observed at 1 to 0 ppm, and it was proved that homopolymerization of ethylene glycol dimethacrylate or trimethylol propane trimethacrylate took place. Accordingly, it was obvious that a vinyl compound having a polythioether compound, as obtained in Example 1, was not obtained.

TABLE 1

| | Polyene compound (A) (parts) | Polythiol compound (B) (parts) | (A)/(B) (functional equivalent ratio) | Catalyst (parts) | Reaction solvent | Temperature (°C.) | Time (hours) | Conversion (%) Vinyl group | Conversion (%) Thiol group | Viscosity (cP) | Storage stability |
|---|---|---|---|---|---|---|---|---|---|---|---|
| Example 1 | EGDMA 700 | EGDTG 300 | 2.5 | Diethylmethylamine 2 | Not added | 40 | 10 | 39.2 | 98.9 | 180 | A |
| Example 2 | EGDMA 900 | TMPTTG 100 | 10.8 | Diethylmethylamine 10 | Not added | 40 | 4 | 9.0 | 99.5 | 150 | A |
| Example 3 | TMPTA 750 | EGDTG 250 | 3.2 | Dimethylethylamine 2 | Not added | 25 | 5 | 31.3 | 98.8 | 400 | A |
| Example 4 | DEGDMA 700 | EGDTG 300 | 2.0 | Diethylmethylamine 10 | Not added | 40 | 8 | 49.7 | 99.0 | 200 | A |
| Example 5 | EGDMA 730 | PETTG 270 | 5.9 | Diethylmethylamine 10 | Not added | 40 | 6 | 16.2 | 99.5 | 270 | A |
| Example 6 | EDMAM 759 | TMPTTG 250 | 3.6 | Diethylmethylamine 10 | Not added | 40 | 18 | 27.1 | 99.2 | 600 | A |
| Comparative Example 1 | EGDMA 700 | EGDTG 300 | 2.5 | — | Not added | 40 | 10 | 67.9 | 50.2 Gelation | — | B |
| Comparative | EGDMA 480 | PETTG 520 | 2.0 | — | Not added | 40 | 8 | 75.0 | 70.2 Forma- | — | B |

TABLE 1-continued

| | Polyene compound (A) (parts) | Polythiol compound (B) (parts) | (A)/(B) (functional equivalent ratio) | Catalyst (parts) | Reaction solvent | Temperature (°C.) | Time (hours) | Conversion (%) Vinyl group | Conversion (%) Thiol group | Viscosity (cP) | Storage stability |
|---|---|---|---|---|---|---|---|---|---|---|---|
| Example 2 | | | | | | | | | tion of gel | | |
| Comparative Example 3 | TMPTMA 620 | EGDTG 380 | 1.5 | Diethylmethylamine 10 | Not added | 40 | 6 | 92.8 | 82.0 Formation of gel | — | B |

Note
EGDMA: ethylene glycol dimethacrylate
EGDTG: ethylene glycol diethioglycolate
TMPTTG: trimethylolpropane trithioglycolate
TMPTA: trimethylolpropane triacrylate
DEGDMA: diethylene glycol dimethacrylate
TMPTMA: trimethylolpropane trimethacrylate
EDMAM: ethylene dimethacrylamide
PETTG: pentaerythritol tetrathioglycolate
[ ]: the thiol group was analyzed by Raman spectroscopy

EXAMPLE 7

In 100 parts of the polymerizable vinyl compound having a polythioether skeleton, obtained in Example 1, was incorporated 0.2 part of azobisisobutyronitrile. The resultant solution was cast in a mold comprising an ethylene/vinyl acetate resin gasket and two glass sheets, and heated at 30° C. for 2 hours and at 35° C. for 10 hours in a hot air furnace. Then, the temperature was evelated to 80° C. over a period of 8 hours. Then, the gasket and mold were disassembled, and a cured product having a thickness of 3 mm was taken out. The obtained cured product was heated at 120° C. for 2 hours to effect annealing. A colorless transparent cured product was obtained.

The physical properties of the cured product are shown in Table 2.

EXAMPLES 8 THROUGH 141

Polymerization was carried out in the same manner as described in Example 7 except that the polymerizable vinyl compounds having a polythioether skeleton, obtained in Examples 2, 4, 5 and 6, were used in Example 8, 9, 10 and 11, respectively, and the radical polymerization initiator was used in an amount shown in Table 2.

The physical properties of the obtained cured products are shown in Table 2.

COMPARATIVE EXAMPLE 4

In 700 parts of ethylene glycol dimethacrylate was incorporated 300 parts of ethylene glycol thiodiglycolate to obtain a solution, and 0.5 part of azobisisobutyronitrile was further incorporated in the solution. Then, a polymerized cured product was prepared according to the same procedures as described in Example 9. The physical properties of the cured product are shown in Table 2.

COMPARATIVE EXAMPLE 5

In 620 parts trimethylolpropane trimethacrylate was incorporated 380 parts of ethylene glycol thiodiglycolate to obtain a solution, and 2 parts of benzoyl peroxide was further incorporated in the solution. A polymerized cured product was obtained according to the same procedures as in Comparative Example 4. The physical properties of the cured product are shown in Table 2.

TABLE 2

| | Initiator (parts per 100 parts of vinyl compound) | Appearance of cured product | Appearance on formation of reflection-preventing coating | Hardness | Light resistance |
|---|---|---|---|---|---|
| Example 7 | Azobisisobutyronitrile 0.2 | A | Not colored | 35 | A |
| Example 8 | Benzoyl peroxide 0.3 | A | Slightly colored | 44 | A |
| Example 9 | Azobisisovaleronitrile 0.5 | A | Not colored | 28 | A |
| Example 10 | t-Butyl peroxypivalate 0.3 | A | Not colored | 42 | A |
| Example 11 | Azobiscyclohexane-carbonitrile 0.6 | A | Not colored | 37 | A |
| Comparative Example 4 | Azobisisobutyronitrile 0.5 | C | Changed to black with surface roughening | 41 | C |
| Comparative Example 5 | Benzoyl peroxide 0.2 | C | Changed to black with surface roughening | 48 | C |

EXAMPLE 12

In 10 parts of the polymerizable vinyl compound having a polythioether skeleton, obtained in Example 3, was incorporated 0.01 part of benzoin isopropyl ether, and the resultant solution was aerated in vacuo and cast in a thickness of 0.2 mm on a glass sheet having a size of 10 cm x 10 cm. The cast solution was irradiated with 0.65 J/cm² of ultraviolet rays from a metal halide lamp located above the glass sheet for 11 seconds. A colorless, transparent and very hard cured resin layer was obtained. The physical properties of the cured product are shown in Table 3.

COMPARATIVE EXAMPLE 6

In 20 parts of trimethylolpropane triacrylate was incorporated 25 parts of ethylene glycol dithioglycolate to obtain a solution, and 1.35 parts of benzoin was further incorporated in the solution. A cured resin layer was prepared in the same manner as described in Example 12 except that conditions shown in Table 3 were adopted. The physical properties of the cured product are shown in Table 3.

In the Raman spectrum, the absorption of thiol groups at 1,570 cm$^{-1}$ disappeared.

TABLE 3

|  | UV initiator (% by weight based on vinyl compound) | Irradiation time (seconds) | Appearance of cured product | Appearance on formation of reflection-preventing coating | Hardness | Light resistance |
|---|---|---|---|---|---|---|
| Example 12 | Benzoin propyl ether 1.0 | 11 | A | Faintly colored in yellow | 45 | A |
| Comparative Example 6 | Benzoin 3.0 | 13 | C | Colored in black with surface roughening | 42 | C |

EXAMPLE 13

A two liter separable flask equipped with a stirrer and a dropping funnel was charged with 750 parts of ethylene glycol dimethacrylate, and 2 parts of diethylamine was added with stirring to form a solution. Then, 250 parts of ethylene glycol dithioglycolate was added dropwise to the solution over a period of 30 minutes. Stirring was conducted at room temperature until generation of heat stopped. After stopping of generation of heat, the reaction mixture was stirred at 40° C. for 10 hours. After termination of the reaction, 50 parts of an inorganic adsorbent for strongly basic adsorption (kyoward 700SL, supplied by Kyowa Kagaku Kogyo K.K.) was added to remove diethylamine. The adsorbent was removed by filtration to obtain a liquid polymerizable prepolymer.

The following $^1$H-NMR spectrum data were obtained with respect to the so-obtained liquid polymerizable prepolymer:

1.2–1.35 ppm (multiplet, α-methyl proton formed by addition of β-methylene of methacryloyl to thiol), 1.9–2.03 ppm (doublet, α-methyl proton of methacryloyl), 2.5–3.1 ppm (multiplet, methine proton and β-methylene proton adjacent to α-methyl proton formed by addition of β-methylene of methacryloyl to thiol), 3.23–3.33 ppm (methylene proton adjacent to thiol of ethylene dithiopropionate), 4.3–4.5 ppm (ethoxy protons of ethylene glycol dimethacrylate and ethylene dithiopropionate), 5.5–6.2 ppm (β-methylene proton of methacryloyl)

The conversion of the vinyl group derived from methacryloyl was 34.8% determined from the integration curve of $^1$H-NMR and this conversion was well in agreement with the theoretical conversion of 35.2% based on the presumption that 100% of the thiol group was reacted. When the thiol group in the liquid polymerizable prepolymer was determined by titration (Volhard method), it was found that the conversion of the thiol group was 99.2% and the residual thiol group was substantially zero.

From the foregoing results, it was obvious that a liquid polymerizable prepolymer having a polythioether skeleton was obtained.

EXAMPLES 14 THROUGH 20

The addition reaction was carried out in the same manner as described in Example 13 except that the polyene compound, polythiol compound, basic catalyst, addition reaction temperature and addition reaction time were changed as shown in Table 4. The results are shown in Table 4.

The results showed that liquid polymerizable prepolymers having substantially a polythioether skeleton were obtained.

COMPARATIVE EXAMPLES 7 THROUGH 9

The addition reaction were carried out in the same manner as described in Example 13 except that conditions were changed as shown in Table 4. The results are shown in Table 4.

TABLE 4

|  | Polyene compound (parts) | Polythiol compound (parts) | Polyene/polythiol functional group equivalent ratio | Catalyst (parts) | Reaction temperature (°C.) | Reaction time (hours) | Conversion of thiol group (%) | Viscosity (cP) | Storage stability |
|---|---|---|---|---|---|---|---|---|---|
| Example 13 | EGDMA 750 | EGDTG 250 | 3.2 | DEA 2 | 40 | 10 | 99.2 | 150 | A |
| Example 14 | NPGDA 900 | EGDTG 100 | 8.9 | DEA 1 | 40 | 8 | 99.4 | 75 | A |
| Example 15 | HDMA 800 | EGDTG 200 | 3.3 | DEA 2 | 40 | 5 | 99.5 | 100 | A |
| Example 16 | TMPTA 800 | EGDTG 200 | 4.1 | DMA 2 | 25 | 6 | 99.8 | 200 | A |
| Example 17 | EGDMA 700 | TMPTTG 300 | 2.8 | DMA 1 | 30 | 8 | 99.7 | 350 | A |
| Example 18 | TMPTMA 700 | EGDTG 300 | 2.2 | DMA 1 | 40 | 8 | 99.6 | 400 | A |
| Example 19 | EGDMA 730 | PETTG 270 | 3.9 | DEA 1 | 40 | 6 | 99.5 | 250–260 | A |
| Example 20 | EGDMA 730 | PETTG 250 DMPOL 20 | 3.6 | DEA 1 | 40 | 5 | 99.3 | 300 | A |
| Comparative Example 7 | HDMA 600 | TMPTTG 400 | 1.4 | DEA 1 | 25 | 10 | 99.4 | Gel contained | B |
| Comparative Example 8 | EGDMA 940 | EGDTG 60 | 15 | DEA 2 | 50 | 2 | 99.5 | 40 | B |
| Comparative | EGDMA 750 | TMPTTG 250 | 3.6 | — | 50 | 10 | 52.2 | 150 | B |

TABLE 4-continued

| | Polyene compound (parts) | Polythiol compound (parts) | Polyene/polythiol functional group equivalent ratio | Catalyst (parts) | Reaction temperature (°C.) | Reaction time (hours) | Conversion of thiol group (%) | Viscosity (cP) | Storage stability |
|---|---|---|---|---|---|---|---|---|---|
| Example 9 | | | | | | | | | |

EGDMA: Ethylene glycol dimethacrylate
TMPTA: Trimethylolpropane triacrylate
TMPTMA: Trimethylolpropane trimethacrylate
NPGDA: Neopentyl glycol diacrylate
NPGDMA: Neopentyl glycol dimethacrylate
HDMA: Hexamethylene glycol dimethacrylate
DMPOL: 2,3-Dimercapto-1-propanol
EGDTG: Ethylene glycol dithioglycolate
TMPTTG: Trimethylolpropane trithioglycolate
PETTG: Pentaerythritol tetrathioglycolate
DEA: Diethylamine
DMA: Diethylmethylamine

EXAMPLE 21

In 100 parts of the liquid polymerizable prepolymer obtained in Example 13 was incorporated 0.2 part of azobisisobutyronitrile to obtain a solution, and the solution was cast in a mold comprising an ethylenevinyl acetate resin gasket and two glass sheets and heated at 30° C. for 2 hours and at 35° C. for 10 hours in a hot air furnace. Then, the temperature was elevated to 80° C over a period of 8 hours. Then, the gasket and mold were disassembled, and a cured product was taken out. The obtained cured product was heated at 120° C. for 2 hours to effect annealing. A colorless transparent cured product was obtained.

The physical properties of the cured product are shown in Table 5.

EXAMPLES 22 THROUGH 28 AND COMPARATIVE EXAMPLES 10 THROUGH 12

Polymerization was carried out in the same manner as described in Example 21 except that the prepolymers obtained in Examples 14 through 20 and Comparative Examples 7 through 9 were used and the radical polymerization initiator was used in an amount shown in Table 5.

The physical properties of the obtained cured products are shown in Table 5.

EXAMPLE 29

By using the apparatus described in Example 13, reaction was carried out in the same manner as described in Example 13 except that 660 parts of ethylene glycol dimethacrylate and 340 parts of ethylene glycol dithioglycolate were used (the functional group equivalent ratio of the polyene compound to the polythiol compound was 2), whereby a polymerizable prepolymer having a viscosity of 600 cP was obtained. The conversion of the thiol was 99.3%. Then, 50 parts of this prepolymer was mixed with 40 parts of a caprolactone-modified polyfunctional polyacrylate (DPCA-20 supplied by Nippon Kayaku K.K.), 0.2 part of 2,2-azobis(2,4-dimethylvaleronitrile) and 0.1 part of azobisisobutyronitrile to form a solution. Then, curing was carried out according to the heating pattern described in Example 21 to obtain a colorless transparent cured product having no polymerization unevenness. The Abbe number of the cured product was 54, the refractive index was 1.520, the hardness was 34 and the light transmission was 91%. The impact resistance, heat resistance, dyeability and light resistance were good (grade A).

We claim:

1. A polymerizable vinyl compound having a polythioether skeleton, which is prepared by addition-reaction (1) a polyene compound represented by the following general formula (I):

TABLE 5

| | | Physical properties of cured product | | | | | | | |
|---|---|---|---|---|---|---|---|---|---|
| | Initiator (parts) | Polymerization unevenness | Refractive index | Hardness | Abbe number | Light transmission (%) | Impact resistance | Heat resistance | Dyeability | Light resistance |
| Example 21 | AIBN 0.2 | A | 1.527 | 32 | 52 | 90 | A | A | A | A |
| Example 22 | ABN-V 0.3 | A | 1.516 | 38 | 51 | 90 | A | A | A | A |
| Example 23 | BPO 0.6 | A | 1.504 | 27 | 55 | 91 | A | A | A | A |
| Example 24 | AIBN 0.3 | A | 1.523 | 35 | 54 | 91 | A | A | A | A |
| Example 25 | AIBN 0.3 | A | 1.527 | 32 | 53 | 90 | A | A | A | A |
| Example 26 | ABN-V 0.2 | A | 1.507 | 30 | 52 | 91 | A | A | A | A |
| Example 27 | ABN-V 0.3 | A | 1.529 | 38 | 53 | 91 | A | A | A | A |
| Example 28 | ABN-V 0.2 AIBN 0.1 | A | 1.530 | 38 | 52 | 90 | A | A | A | A |
| Comparative Example 10 | AIBN 0.5 | C | 1.515 | 20 | 52 | 90 | A | C | C | A |
| Comparative Example 11 | ABN-V 0.4 | A | 1.492 | 40 | 58 | 92 | C | A | A | A |
| Comparative Example 12 | BPO 0.6 | C | 1.528 | 27 | 53 | 90 | A | A | C | A |

Note
AIBN: Azobisisobutyronitrile
ABN-V: 2,2-Azobis(2,4-dimethylvaleronitrile)
BPO: Benzoyl peroxide A-X$_m$       (I)

wherein X stands for (a)

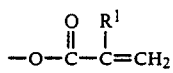

or (b)

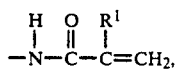

A stands for a polyvalent aliphatic or alicyclic hydrocarbon residue, or

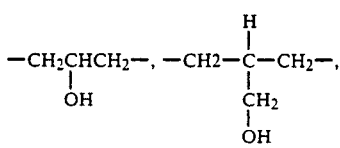

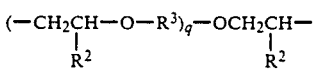

or

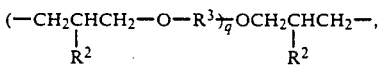

R$^1$ stands for H or CH$_3$, R$^2$ stands for H, an aliphatic hydrocarbon residue or OH, R$^3$ stands for an aliphatic or alicyclic hydrocarbon residue which may contain a halogen atom, and m and q are integers of m $\geq$ 2 and q $\geq$ 1, with (2) at least one polythiol compound selected from the group consisting of those which are represented by the following general formulae (II) and (IV):

R$^4$—SH)$_r$       (II)

wherein R$^4$ stands for an organic group consisting of an aliphatic or alicyclic hydrocarbon, and r is an integer of from 2 to 4,

wherein R$^9$ stands for a substituted or unsubstituted aliphatic polyhydric alcohol residue having 2 to 20 carbon atoms, which may have an OH group, u is an integer of 1 or 2, and v is an integer of form 2 to 4, in the presence of a basic catalyst under such a condition that the ratio of the total number of vinyl groups in the polyene compound to the total number of thiol groups in the polythiol compound is at least 2; the terminal groups of said polymerizable vinyl compound being X.

2. A polymerizable vinyl compound according to claim 1 wherein the polyene compound is represented by the following general formula (III):

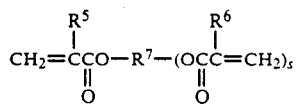

wherein R$^5$ and R$^6$, which may be the same or different, stand for H or a CH$_3$ group, R$^7$ stands for a substituted or unsubstituted aliphatic polyhydric alcohol residue or substituted or unsubstituted polyalkylene-ether polyol residue having 2 to 20 carbon atoms, which may have an OH group, and s is an integer of 1 or 2.

3. A polymerizable vinyl compound according to claim 1 wherein the ratio of the total number of vinyl groups to the total number of thiol groups is in the range of from 2 to 20.

4. A polymerizable vinyl compound according to claim 1 wherein the basic catalyst is a phosphine compound or an amine compound.

5. A polymerizable vinyl compound according to claim 1 wherein the basic catalyst is used in an amount of 0.01 to 3% by weight based on the total weight of the polyene compound and the polythiol compound.

6. A polymerizable vinyl compound according to claim 1 wherein the polymerizable vinyl compound having a polythioether skeleton possesses a viscosity of from 10 to 30,000 cP at 25° C.

* * * * *